United States Patent
Matsuo

(10) Patent No.: US 10,359,405 B2
(45) Date of Patent: Jul. 23, 2019

(54) ANALYZING-DEVICE CONTROLLER

(71) Applicant: SHIMADZU CORPORATION, Kyoto-shi, Kyoto (JP)

(72) Inventor: Kiriko Matsuo, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/317,542

(22) PCT Filed: Jun. 12, 2014

(86) PCT No.: PCT/JP2014/065549
§ 371 (c)(1),
(2) Date: Dec. 9, 2016

(87) PCT Pub. No.: WO2015/189945
PCT Pub. Date: Dec. 17, 2015

(65) Prior Publication Data
US 2017/0115261 A1    Apr. 27, 2017

(51) Int. Cl.
*G01N 30/88* (2006.01)
*G01N 30/24* (2006.01)
(Continued)

(52) U.S. Cl.
CPC .......... *G01N 30/88* (2013.01); *G01N 30/24* (2013.01); *G01N 30/86* (2013.01);
(Continued)

(58) Field of Classification Search
CPC ................ G01N 30/88; G01N 30/24
See application file for complete search history.

(56) References Cited

U.S. PATENT DOCUMENTS

| 2013/0333490 A1* | 12/2013 | Tanoue | G01N 30/24 73/863.01 |
| 2014/0157878 A1* | 6/2014 | Ohashi | G01N 30/466 73/61.56 |
| 2015/0107334 A1* | 4/2015 | Hunter | G01N 30/16 73/23.41 |

FOREIGN PATENT DOCUMENTS

| JP | 1-250060 A | 10/1989 |
| JP | 03-063566 A | 3/1991 |

(Continued)

OTHER PUBLICATIONS

English Translation for JP 03-063566A and JP2011-099679A.*
(Continued)

*Primary Examiner* — Christine A Enad
(74) *Attorney, Agent, or Firm* — Sughrue Mion, PLLC

(57) ABSTRACT

A specimen information storage section (361) holds specimen information showing the relationship between a number of specimens to be analyzed and compounds whose quantities need to be determined. An analysis method storage section (362) holds the files of analysis methods created by an administrator. When an operator selects and indicates analysis methods to be used in an analysis, a method information creation processor (32) extracts compound information from the selected analysis methods and creates method information showing the correspondence between the analysis methods and the compounds to be analyzed. When the operator registers the specimen numbers of the analysis targets, a used-method automatic determiner (34) refers to the specimen information and method information to identify a suitable analysis method for each compound in the registered specimens. An analysis schedule creator (35) creates a schedule table in which the specimens and analysis methods are described in order of the analysis. This schedule includes no useless analysis performed using an analysis (Continued)

method which is unsuitable for the analysis concerned. Consequently, the efficiency of the analysis is improved.

3 Claims, 3 Drawing Sheets

(51) Int. Cl.
    *G01N 30/86*     (2006.01)
    *G01N 35/00*     (2006.01)
    *G01N 30/72*     (2006.01)

(52) U.S. Cl.
    CPC ..... *G01N 35/0092* (2013.01); *G01N 30/7233* (2013.01); *G01N 2030/8804* (2013.01); *G01N 2035/0094* (2013.01)

(56) References Cited

FOREIGN PATENT DOCUMENTS

| JP | 9-329604 A | 12/1997 |
|---|---|---|
| JP | H10-019901 A | 1/1998 |
| JP | 2010-025587 A | 2/2010 |
| JP | 2011-099679 A | 5/2011 |
| WO | 2013/011818 A1 | 1/2013 |

OTHER PUBLICATIONS

Written Opinion for PCT/JP2014/065549 dated Sep. 16, 2014. [PCT/ISA/237].
"Mesoddo Kaihatsu No Kouritsuka (Improving the Efficiency of Method Development)", Shimadzu Corporation, [accessed on May 29, 2014], <URL:http://www.an.shimadzu.co.jp/hplc/support/lib/lctalk/74/74tec.htm>.
International Search Report for PCT/JP2014/065549 dated Sep. 16, 2014.
Communication dated Sep. 26, 2017 from the Japanese Patent Office in counterpart application No. 2016-527556.

\* cited by examiner

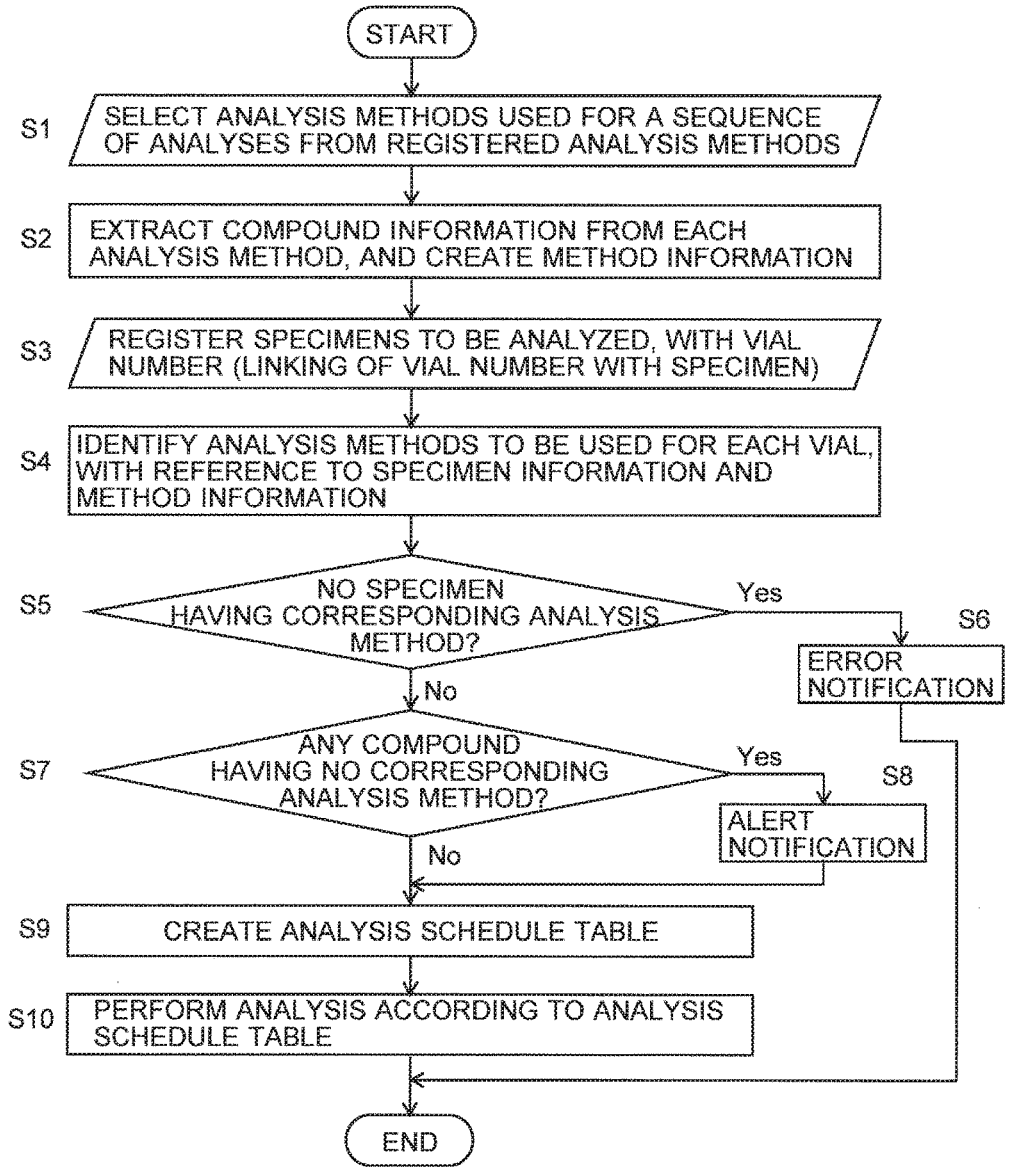

Fig. 4

METHOD INFORMATION

| METHOD NAME | CORRESPONDING COMPOUND |
|---|---|
| Method_A | C3 |
| Method_C | C2 |
| ... | ... |
| Method_M | C1 |

Fig. 5A

SAMPLE REGISTRATION INFORMATION

| SPECIMEN No. | VIAL No. |
|---|---|
| U0001 | 1 |
| U0002 | 2 |
| ... | ... |
| U1234 | 10 |

Fig. 5B

SAMPLE PLATE

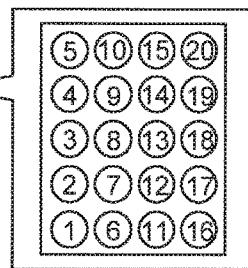

Fig. 6A

CONVENTIONAL

| VIAL No. | USED METHOD |
|---|---|
| 1 | Method_A |
| 1 | Method_C |
| 1 | Method_M |
| 2 | Method_A |
| 2 | Method_C |
| 2 | Method_M |
| 10 | Method_A |
| 10 | Method_C |
| 10 | Method_M |

ORDER OF ANALYSIS ↓

Fig. 6B

PRESENT INVENTION

| VIAL No. | USED METHOD |
|---|---|
| 1 | Method_C |
| 1 | Method_M |
| 2 | Method_A |
| 2 | Method_C |
| 10 | Method_M |

ORDER OF ANALYSIS ↓

ANALYZING-DEVICE CONTROLLER

CROSS REFERENCE TO RELATED APPLICATIONS

This application is a National Stage of International Application No. PCT/JP2014/065549 filed Jun. 12, 2014, the contents of all of which are incorporated herein by reference in their entirety.

TECHNICAL FIELD

The present invention relates to a controller for an analyzing device, such as a liquid chromatograph, gas chromatograph, liquid chromatograph mass spectrometer, or gas chromatograph mass spectrometer and particularly, to a controller suitable for an automatic analyzing device which continuously performs an analysis for a plurality of samples using the combination of an auto-sampler which automatically selects and collects each sample from a number of prepared samples and an analyzing device which analyzes the sample collected with the auto-sampler.

BACKGROUND ART

In an analyzing device, represented by a liquid chromatograph (LC) or gas chromatograph (GC), an analysis for a sample is conducted according to preset analysis conditions, and a qualitative and/or quantitative determination (or similar analysis) is performed by processing the data according to preset data-analyzing and processing conditions. For example, in the case of the liquid chromatograph, the analysis conditions include the flow velocity of the mobile phase, gradient conditions, and column temperature, while the data-analyzing and processing conditions include the retention time, peak-waveform-processing parameters, and calibration curves. In the following descriptions, the "analysis conditions" should basically be regarded as inclusive of the data-analyzing and processing conditions.

In recent years, with the improvements in the performance and functions of analyzing devices, the analysis conditions have been increasingly complex, with a large number of items to be set by users in relation to those conditions. An appropriate setting of the analysis conditions is essential to obtain correct results of the measurement and analysis. To this end, an administrator who is familiar with the analyzing task and has a broad amount of expertise is required to determine those conditions. However, in research institutes or contracted analysis businesses which need to perform measurements and analyses for an enormous number of samples, it is often the case that an operator with no expertise pertaining to the analyses and related tasks takes charge of the actual analyzing task. In order for such an operator to even efficiently perform the analyzing task with no mistakes, analyzing devices offered in recent years have been provided with packages of analysis conditions for performing a sequence of measurement and data-analyzing processes, requiring analysis operators to merely select one package to be used in the analysis.

For example, in Patent Literature 1 and other documents, a set of analysis conditions packaged in the previously described manner is called the "analysis method", while a data file for computers in which those conditions are described is called the "analysis method file".

In general, optimum analysis conditions differ from compound to compound (although the same set of analyzing conditions can in some cases yield almost equally accurate results for a plurality of compounds). Accordingly, in the contracted analysis businesses or similar institutions mentioned earlier, the administrator normally prepares appropriate analysis methods beforehand for various compounds to be analyzed, and stores the analysis method files in a storage device in a computer (see Non Patent Literature 1 or other documents). When initiating an automatic analysis for a number of specimens, the operator referring to an instruction (or similar document) selects one or more analysis methods from the registered analysis methods and issues a command for initiating the analysis.

Such an analyzing technique using a conventional analyzing device has the following problem.

For example, consider the case where the specimens are subjects' samples of blood or urine, and the quantity of a known kind of drug or metabolite contained in each specimen needs to be determined. In such a test, it is often the case that, although the kinds of target compounds are limited, the kind of compound whose quantity needs to be determined changes from specimen to specimen. According to the previously described conventional technique, an analysis using the initially selected analysis method is performed for each specimen, i.e. for all specimens exhaustively. This means that some specimen is subjected to an analysis which uses an analysis method prepared for a compound that is not the target of the quantitative determination for that specimen. Such an analysis is practically useless and merely wastes the specimen. It is also a waste of time used for the analysis as well as a waste of mobile phase and carrier gas in the case of the LC or GC.

Furthermore, according to the previously described conventional technique, when a plurality of compounds whose quantities need to be determined are contained in one specimen, it is basically necessary to repeat a plurality of times the analysis for the same specimen using different analysis methods, so that the analysis requires a considerable amount of time. In the case of an LC-MS or GC-MS using a tandem quadrupole mass spectrometer as the detector, if the retention times of the plurality of compounds contained in one specimen are close to each other, it is possible to repeat the cycle of sequentially executing MRM (multiple reaction monitoring) transitions (i.e. combinations of the mass-to-charge ratio of the precursor ion and that of the product ion) corresponding to the respective compounds within the same time range, create a chromatogram for each MRM transition ("extracted ion chromatogram"), and perform the quantitative determination. By this method, the quantities of a plurality of compounds contained in one specimen can be determined by a single analysis. However, since the detection process for the plurality of compounds needs be completed within the limited length of time during which the target compound is being eluted, the detection time per one compound becomes short, so that the sensitivity becomes low.

For example, in the case of the LC, this decrease in the detection sensitivity can be avoided by performing a gradient analysis so as to improve the separation characteristics of the column and thereby enable the detection of each compound within a specific time range where no other overlapping compound is present. However, this method also results in a longer period of time required for one analysis; in some cases, the gradient analysis requires almost the same amount of time as the normal analysis performed two times for the same specimen. Furthermore, an analysis method prepared for a gradient analysis is normally unusable for an analysis of a specimen containing other compounds; the analysis method is dedicated for a specimen containing a specific combination of compounds, and therefore, is unsuitable for an exhaustive analysis. Needless to say, the task of preparing the analysis method is extremely complex and time-consuming.

CITATION LIST

Patent Literature

Patent Literature 1: WO 2013/011818 A
Non Patent Literature 1: "Mesoddo Kaihatsu No Kouritsuka (Improving the Efficiency of Method Development)", Shimadzu Corporation, [accessed on May 29, 2014], the Internet

SUMMARY OF INVENTION

Technical Problem

The present invention has been developed in view of the previously described problem, and its primary objective is to provide an analyzing-device controller capable of performing an analysis with no burden on an operator who has a poor amount of expertise pertaining to the analysis, with a short period of time required for the analysis, and with a decreased use of the specimen, mobile phase, carrier gas and other substances consumed in the analysis.

Solution to Problem

The present invention developed for solving the previously described problem is an analyzing-device controller for controlling an operation of an analyzing device for performing a continuous analysis for a plurality of specimens each of which contains one or a plurality of compounds, the controller including:

a) a specimen information obtainer for obtaining, for each specimen to be analyzed, specimen information showing one or a plurality of possible target compounds contained in the specimen;

b) a method information obtainer for obtaining, for each analysis method in which analysis conditions for performing an analysis are described, a piece of information included in the analysis method, this information showing a compound assumed in an analysis using the analysis method concerned, and for creating method information linking the compound with the analysis method;

c) an optimum method determiner configured as follows: when a plurality of specimens to be actually analyzed are specified by an operator in a continuous analysis for a plurality of specimens, the optimum method determiner identifies a one or a plurality of target compounds in each of the specified specimens based on the specimen information obtained by the specimen information obtainer, then identifies one or a plurality of analysis methods for the one or the plurality of target compounds identified for each of the specimens based on the method information created by the method information obtainer, and creates combination information linking the plurality of specimens specified by the operator with one or a plurality of analysis methods suitable for use in an analysis for each of the plurality of specimens, and the controller conducts a continuous analysis for a plurality of specimens based on the information created by the optimum method determiner.

In the analyzing-device controller according to the present invention, the analyzing device is not limited to any specific type; it may be any device capable of performing an analysis for a compound contained in a specimen (sample). Typical examples include liquid chromatographs (LC), gas chromatographs (GC), liquid chromatograph mass spectrometers (LC-MS) and gas chromatograph mass spectrometers (GC-MS). An analysis method used in these types of analyzing devices includes analysis conditions concerning the separation performance in the chromatograph, such as the flow velocity of the mobile phase and the column temperature in the case of the LC. In the case of the LC-MS, GC-MS or similar device, the analysis method includes analysis conditions in the mass spectrometer, such as the scan rate and scan range (mass-to-charge-ratio range) in the case of performing a scan measurement. In the case where the mass spectrometer is a tandem quadrupole mass spectrometer, the analysis method includes, for example, the collision energy and the MRM transition.

In order to perform a continuous analysis for a plurality of specimens, the aforementioned types of analyzing devices include a sample supply system (which is generally called the auto-sampler, or by other names) which automatically selects one of the prepared specimens, collects a fraction of the selected specimen, and provides it for the analysis. The analyzing device may also include a data processor for identifying the compound and/or determining its quantity by analyzing and processing the data obtained by the analysis performed for the specimen. In the case where the analyzing device includes the data processor, the analysis method includes the data-analyzing and processing conditions to be used in the data processing.

The specimen information used in the analyzing-device controller according to the present invention may be prepared by a business or institution which actually carries out an analysis using the analyzing device, or the information may be externally provided, i.e. from other businesses or institutions than the business or institution which actually carries out the analysis using the analyzing device. For example, when a test on a large number of specimens is commissioned by a medical institution, the specimen information is prepared by that medical institution.

The specimen information may be stored in a storage device provided as a part of the present analyzing-device controller, or it may be stored in an external storage device which can be seamlessly accessed from the present analyzing-device controller. In the former case, the "specimen information obtainer" in the analyzing-device controller according to the present invention is a means for reading the information concerned from the internal storage device. In the latter case, the "specimen information obtainer" in the analyzing-device controller according to the present invention is a means for accessing the external storage device through communication lines to read and receive the information concerned.

Analysis methods are normally prepared in a business or institution which performs an analysis using the present analyzing device, by an administrator having expertise on the analysis and a high level of authority concerning the analysis. Needless to say, it is also possible for manufacturers of the analyzing device or similar institutions to develop analysis methods suitable for analyzing specific kinds of specimens, and provide those methods to users, i.e. businesses and institutions.

If the analyzing device is an LC, GC, LC-MS or GC-MS mentioned earlier, and if the quantity of the target compound is determined based on a chromatogram, the analysis method includes a calibration curve for quantitative determination. In principle, one calibration curve corresponds to one specific compound. Accordingly, an analysis method which includes a calibration curve is normally dedicated to one specific compound, and therefore, contains information concerning the assumed compound, such as the compound name.

Accordingly, for example, when a plurality of analysis methods which may possibly be used in an analysis for a plurality of specimens are specified, the method information obtainer reads compound information from those analysis methods and creates method information showing the correspondence between the analysis methods and the compounds. It is also possible to create method information showing the correspondence between the analysis methods and the compounds for all of the created or given analysis methods, regardless of which analysis methods are specified.

In the case where a continuous analysis for a number of specimens is performed using an auto-sampler, the correspondence relationship between the position of the vial on the sample plate set in the auto-sampler and the information for identifying the specimen to be analyzed (e.g. the specimen number) is specified by an operator in charge of the analyzing task. After the set of specimens to be analyzed is fixed by such a specifying operation or similar task, the optimum method determiner identifies one or a plurality of target compounds in each specimen to be analyzed, based on the specimen information. Additionally, based on the method information, the optimum method determiner identifies the analysis method corresponding to each of the specified target compounds. As a result, for each specimen, the correspondence between that specimen and one or a plurality of analysis methods suitable for use in an analysis of that specimen is revealed. Then, the optimum method determiner creates information showing the revealed combination. This information can be used, for example, as a portion of the information which is generally called an "analysis schedule" or "batch table" that specifies the order of the analyses in a continuous analysis.

In the previously described manner, the analyzing-device controller according to the present invention automatically chooses an analysis method suitable for an analysis of a target compound contained in a specimen which is to be analyzed from a plurality of analysis methods which have been created or specified, and creates information which links the specimen with the analysis method. Accordingly, the situation that an analysis which uses an analysis method that does not correspond the target compound in the specimen concerned is performed on this specimen can be avoided even if an operator who has a poor amount of expertise on the analysis takes charge of the task.

In some cases, there may be no suitable analysis prepared for the analysis of the target compound in the specimen which is to be analyzed. Accordingly, the analyzing-device controller according to the present invention may preferably be configured so that, when the target compounds contained in each of the plurality of specimens specified as the target of the analysis include at least one target compound for which no corresponding analysis method is present and at least one target compound for which a corresponding analysis method is present, an alert notification is made while the analysis for the target compound in the specimen concerned is performed, and when none of the target compounds have a corresponding analysis method, an error notification is made.

According to this configuration, when at least one target compound is contained in the specimen which is to be analyzed, the analysis for that specimen using the analysis method corresponding to that target compound is performed, to eventually obtain the quantitative determination result on that target compound or other useful information. Meanwhile, with the alert notification, the operator can recognize the fact that the analysis for some compound has not been performed due to the absence of the corresponding analysis method. When the analysis has not been performed for any of the target compounds due to the absence of the corresponding analysis methods, the operator can recognize this fact by the error notification. Thus, in any case, the situation that an analysis using an inappropriate analysis method is performed for a target compound in the specimen can be avoided.

The analyzing-device controller according to the present invention may further include an analysis method integrator configured as follows: when a plurality of analysis methods are linked with the same specimen as a result of the processing performed by the optimum method determiner, the analysis method integrator checks that a portion of the analysis conditions included in each of those analysis methods is common to all analysis methods, and non-identical portions of the analysis conditions do not affect the results of analyses for the plurality of target compounds corresponding to those analysis methods; and if these facts are confirmed, the analysis method integrator combines the analysis conditions included in those analysis methods to create a temporary analysis method corresponding to the plurality of target compounds.

Specifically, for example, in the case where the analyzing device is a liquid chromatograph, if the separation conditions in the LC (e.g. the flow velocity of the mobile phase) are common to a plurality of analysis methods, and if the retention times of the target compounds are not overlapped, the separation conditions included in those analysis methods can be combined to create a temporary analysis method corresponding to those target compounds. This reduces the number of times of the analysis to be performed for one specimen, making it possible to achieve a shorter analysis time and an additional reduction in the use of the specimen, mobile phase and other consumed substances.

The analyzing-device controller according to the present invention may typically be configured in the form of a personal computer equipped with an input unit and display unit, with a predetermined control software program previously installed. In this case, the method information obtainer and the optimum method determiner may be implemented as functions realized by the control software program running on the computer.

ADVANTAGEOUS EFFECTS OF THE INVENTION

With the analyzing-device controller according to the present invention, it is possible to avoid the situation that an analysis for a specimen is performed using an analysis method that does not correspond the target compound in the specimen concerned. Useless analyses are thereby prevented, so that the analysis time is shortened and the efficiency of the analyzing task is improved. The use of the specimen, mobile phase and other consumed substances can be decreased, whereby the cost of the analysis can be reduced. The fact that the operator in charge of the task does not need to have a high amount of expertise on the analysis is also advantageous for the cost reduction of the analysis. Incorrect operations or similar errors which cause a delay in the analyzing task or provision of an inappropriate result can also be prevented.

BRIEF DESCRIPTION OF DRAWINGS

FIG. 2 is a flowchart showing operator's tasks as well as the processing operations performed in response to those tasks in the LC-MS analyzing system of the present embodiment.

FIG. 3 is one example of the specimen information in the LC-MS analyzing system of the present embodiment.

FIG. 4 is one example of the method information in the LC-MS analyzing system of the present embodiment.

FIGS. 5A and 5B are one example of the sample registration information in the LC-MS analyzing system of the present embodiment.

FIGS. 6A and 6B illustrate the difference between an analysis schedule table used in a conventional system and one used in the LC-MS analyzing system of the present embodiment.

DESCRIPTION OF EMBODIMENTS

Figure 1:
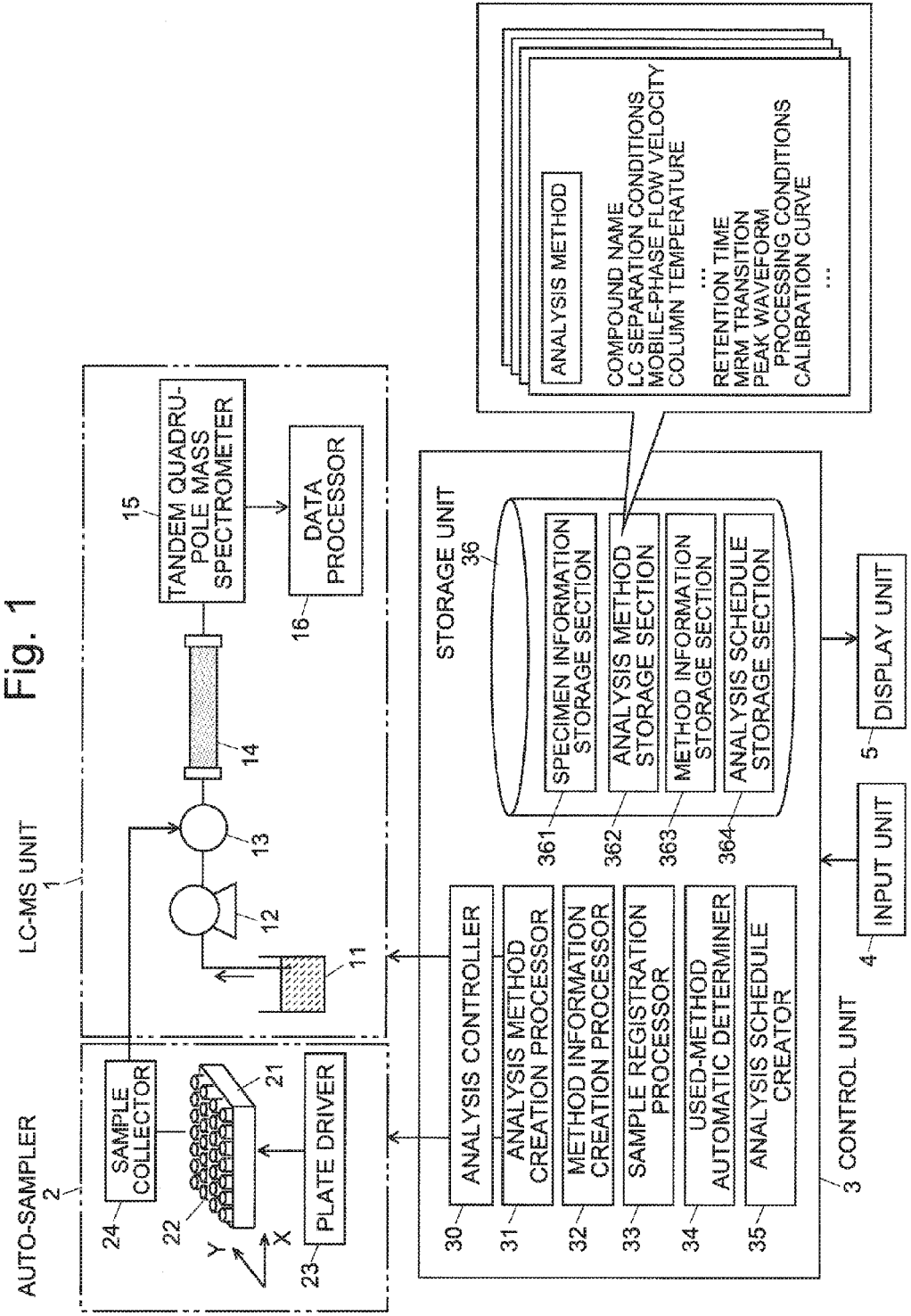
FIG. 1 is a schematic configuration diagram of one embodiment of an LC-MS analyzing system using an analyzing-device controller according to the present invention.

One embodiment of an LC-MS analyzing system using an analyzing-device controller according to the present invention is hereinafter described with reference to the attached drawings. FIG. 1 is a schematic configuration diagram of the LC-MS analyzing system according to the present embodiment.

This LC-MS analyzing system includes: a liquid chromatograph mass spectrometer unit (LC-MS unit) 1 which temporally separates the compounds contained in a sample solution (specimen) and detects those compounds; an auto-sampler 2 which sequentially selects one of a number of previously set vials 22 and supplies the sample solution from the selected vial 22 to the LC-MS unit 1; a control unit 3 which controls the operations of the aforementioned units; and other relevant units.

The LC-MS unit 1 includes: a mobile phase container 11 holding a mobile phase; a pump 12 for drawing the mobile phase from the mobile phase container 1 and supplying it at a substantially constant flow velocity; an injector 13 for injecting a sample solution into the mobile phase; a column 14 for temporally separating the various compounds contained in the sample solution injected into the mobile phase; a tandem quadrupole mass spectrometer 15 which is the detector for sequentially detecting the various compounds separated by the column 14; and a data processor 16 for processing detection signals obtained with the tandem quadrupole mass spectrometer 15.

Although not shown in the figure, the tandem quadrupole mass spectrometer 15 has an atmospheric pressure ion source (e.g. an electrospray ion source), a front quadrupole mass filter for separating the ions generated by the atmospheric pressure ion source according to their mass-to-charge ratios, a collision cell for dissociating the ions passing through the front quadrupole mass filter by collision induced dissociation (or similar technique), a rear quadrupole mass filter for separating the product ions generated by the dissociation in the collision cell according to their mass-to-charge ratios, and a detector for detecting the ions passing through the rear quadrupole mass filter and for producing detection signals according to the amount of ions.

The auto-sampler 2 includes: a tray-shaped sample plate 21 on which a number of vials 22 each of which holds a sample solution are placed; a plate driver 23 for changing the position of the sample plate 21 in the directions of X and Y axes which are orthogonal to each other; and a sample collector 24, which includes a needle, needle-elevating mechanism and other components, for suctioning a predetermined amount of sample solution from the vial 22 located at a predetermined sample-suctioning position. The sample solution collected with the sample collector 24 is sent to the injector 13 in the LC-MS unit 1, to be injected into the mobile phase or disposed of to a disposal section (not shown).

The control unit 3, to which an input unit 4 and display unit 5 serving as the user interface are connected, includes, as its functional blocks, an analysis controller 30 which sends control signals to both of the LC-MS unit 1 and auto-sampler 2 so as to conduct an analysis, as well as an analysis method creation processor 31, method information creation processor 32, sample registration processor 33, used-method automatic determiner 34, analysis schedule creator 35, and storage unit 36. In the storage unit 36, various storage areas are provided, such as a specimen information storage section 361, analysis method storage section 362, method information storage section 363, and analysis schedule storage section 364. The control unit 3 can be configured using a personal computer or higher-performance workstation as a hardware resource, with the functions of the aforementioned blocks realized by running, on that computer, a dedicated control software program previously installed on the same computer. Similarly, the data processor 16 can be configured by running, on a computer, a dedicated processing software program previously installed on the same computer.

The characteristic control operation in the LC-MS analyzing system of the present embodiment is hereinafter described. The following description deals with the case where a contracted analysis business (or similar institution) uses the present LC-MS analyzing system to conduct quantitative determination of specific compounds contained in a number of specimens commissioned from a medical institution (or similar organization).

In this case, the kinds of compounds whose quantities need to be determined in each specimen are decided by the client, i.e. the medical institution (or similar organization). Therefore, the specimen information showing the correspondence relationship between the specimen number and the name of the compound to be analyzed (the name of the compound whose quantity needs to be determined) as shown in FIG. 3 is externally provided (e.g. from the medical institution). This information is taken into the control unit 3 of the present system via memory media or through communication lines (e.g. the Internet), and stored in the specimen information storage section 361 in the storage unit 36. In some cases, one compound to be analyzed is specified for one specimen as shown in the example of FIG. 3, while in other cases two or more compounds to be analyzed are specified.

For example, the kind of specimen, such as blood or urine, is determined beforehand, and the kinds of compounds to be identified are also determined. In the contracted analysis business concerned, an administrator having expertise on the analysis as well as a high level of right to access the system performs an analysis on each compound in the specimen. Based on the analysis result, the administrator experimentally determines, for each compound, the optimum analysis conditions for the quantitative determination of the compound concerned. Then, using the function of the analysis method creation processor 31, the administrator creates an analysis method file in which those analysis conditions are described. The analysis method creation processor 31 stores the analysis method file created by the administrator in the analysis method storage section 362 of the storage unit 36. Preferably, one analysis method should be created for each compound, with each analysis method including an item of information indicating the kind of compound (typically, the compound name). Needless to say, if there is a plurality of compounds that can be analyzed under the same set of analysis conditions with equal levels of accuracy and sensitivity, those compounds can be liked with one analysis method. In this case, a piece of information indicating the kinds of those compounds should be included in that analysis method.

In the LC-MS analyzing system of the present embodiment, as shown in FIG. 1, the analysis method includes various analysis conditions and related parameters in addition to the already mentioned compound name, such as the mobile-phase flow velocity, column temperature, LC separation conditions (e.g. gradient conditions), retention time (i.e. the point in time at which the compound concerned is eluted from the column 14), MRM transition suitable for detecting the compound concerned in the tandem quadrupole mass filter 15, peak waveform processing conditions for detecting a peak originating from the compound concerned on the extracted ion chromatogram, and calibration curve showing the relationship between the concentration and peak area at the compound concerned.

FIG. 2 is a flowchart showing the tasks performed by an operator who actually takes charge of the analysis as well as the processing operations in response to those tasks. Following this flow chart, the operations and processes which are mainly performed before the initiation of the analysis are hereinafter described.

When initiating an analysis, the operator specifies one or more analysis methods to be used in a sequence of analyses for a plurality of specimens, according to the instructions (or the like) prepared by an administrator. Specifically, when the operator using the input unit 4 performs a predetermined operation, the sample registration processor 33 responds to the operation and displays a list of the analysis method files registered in the analysis method storage section 362 on the screen of the display unit 5. Viewing this list, the operator selects and indicates one or more analysis methods to be used (Step S1). Upon receiving this selection and indication, the method information creation processor 32 reads the indicated method files from the analysis method storage section 362 and extracts information on the compound name written in each of those analysis method files. Then, the method information creation processor 32 creates method information which links the compound names with the names of the respective analysis methods ("method file names"), and stores this information in the method information storage section 363 of the storage unit 36 (Step S2).

FIG. 4 shows one example of the method information. This method information includes all method files selected and indicated by the operator in Step S1.

Alternatively, the method information creation processor 32 may also create the method information for all analysis methods stored in the analysis method storage section 362, without requiring the operator to indicate the analysis methods to be used for the analysis in Step S1. Such a method causes no practical problem if the number of analysis methods stored in the analysis method storage section 362 is not very large. It is also possible to divide the analysis methods into groups and allow the operator to select any of those groups so as to simultaneously select and indicate all analysis methods belonging to the indicated group. For example, the analysis methods can be grouped by the purpose of the analysis, e.g. "methods for testing X" or "methods for testing Y", whereby the burden on the operator is decreased and incorrect operations are prevented.

Next, the operator places vials onto the sample plate 21 in the auto-sampler 2, with each vial containing one specimen to be analyzed, and registers through the input unit 4 the correspondence between the vial number specified on the sample plate 21 and the specimen number which identifies each specimen (Step S3). Specifically, for example, the sample plate 21 has vial numbers as shown in FIG. 5B (in the shown example, vial numbers 1-20). For each vial number, the operator specifies the specimen number of the specimen contained in the vial that should be placed at the position having that vial number. Alternatively, for each of the specimen numbers assigned to the specimens to be analyzed, the operator specifies the vial number assigned to the position at which the specimen concerned should be placed. In any case, as a result of such an input, the sample registration information including the specimen numbers linked with the vial numbers is obtained, as shown FIG. 5A.

After the sample registration information is fixed, the used-method automatic determiner 34 refers to the specimen information stored in the specimen information storage section 361 to search for the corresponding compound name for each specimen number registered in the sample registration information. For example, for specimen number "U0001" linked with vial number "1" in the sample registration information, two compound names "C1" and "C2" are located by referring to the specimen information shown in FIG. 3. Subsequently, for each of the identified compounds, the used-method automatic determiner 34 refers to the method information stored in the method information storage section 363 to search for the analysis method file name to be used for the analysis. For example, for compound "C1", the analysis method with a file name of "Method_M" is located by referring to the method information shown in FIG. 4. Similarly, the analysis method with a file name of "Method_C" is located for compound "C2". In this manner, it is revealed that the analysis methods suitable for an analysis of the target compounds contained in the specimen in the vial placed at the position with vial number "1" on the sample plate 21 are "Method_M" and "Method_C". In this manner, for each vial number, the analysis methods suitable for an analysis of the target compounds contained in the specimen in the vial placed at the position indicated by that vial number are revealed (Step S4).

However, it is not always the case that appropriate analysis methods for an analysis of the target compounds in a specific specimen have already been created. It is also possible that the operator makes an error in the selection and indication of the analysis methods or in the selection of the specimens, with the result that no appropriate analysis method is present for any of the target compounds in the plurality of specimens. Therefore, after the process of Step S4 has been completed, the used-method automatic determiner 34 determines whether or not there is no specimen for which the corresponding analysis method has been located (Step S5). If "Yes" (i.e. there is no specimen for which the corresponding analysis method has been located) in Step S5, it is impossible to perform an appropriate measurement and data-analyzing process for any of the specimens. Accordingly, an error notification is shown on the display unit 5 (Step S6) and the entire process is completed. In other words, in this case, no analysis is performed.

In the determination result in Step S5 is "No", the used-method automatic determiner 34 determines whether or not there is any compound for which no corresponding analysis method has been located (Step S7). If the determination result in Step S7 is "No", it means that an appropriate analysis method for the analysis is determined for any target compound in all specimens. Accordingly, the operation proceeds to Step S9. If the determination result in Step S7 is "Yes", it means that there is at least one target compound in one specimen for which no appropriate analysis method is present, while there is also at least one target compound in one compound for which an appropriate analysis method is present. In this situation, the analysis can be carried out for at least one target compound for which an appropriate analysis method is present. Accordingly, an alert notification is shown on the display unit 5 (Step S8), and the operation proceeds to Step S9.

In Step S9, the analysis schedule creator 35 creates an analysis schedule table which contains detailed descriptions of the analyses according to the order of those analyses, and stores it in the analysis schedule storage section 364 in the storage unit 36. The analysis schedule table contains the vial number and the file name of the analysis method used for an analysis of the specimen placed at the position having that vial number, as well as the amount of specimen to be collected (and injected into the LC-MS unit 1) and other relevant information. FIG. 6B partially shows one example of the analysis schedule table. Subsequently, when the operator using the input unit 4 issues a command to initiate the analysis, the analysis controller 30 performs a sequence of continuous analyses according to the analysis schedule table stored in the analysis schedule storage section 364 (Step S10).

In the example of FIG. 6B, the analysis for the specimen contained in the vial placed at the position with vial number "1" is initially performed, including the first analysis according to the analysis method with a file name of "Method_C", followed by the second analysis according to the analysis method with a file name of "Method_M". Subsequently, the analysis for the specimen contained in the vial placed at the position with vial number "2" is performed, including the third analysis according to the analysis method with a file name of "Method_A", followed by the fourth analysis according to the analysis method with a file name of "Method_C".

In order to improve the efficiency of the analysis, it is preferable to collectively perform two or more analyses that can be performed using the same analysis method. In the present example, the analyzing sequence can be modified as follows: Initially, the analysis according to the analysis method "Method_C" is performed for the specimen contained in the vial placed at the position with vial number "1", followed by the analysis for the specimen contained in the vial placed at the position with vial number "2" which is also performed according to the analysis method "Method_C". After that, the analysis for the specimen contained in the vial placed at the position with vial number "1" is once more performed, this time according to analysis method "Method_M", which is followed by the analysis according to analysis method "Method_A" for the specimen contained in the vial placed at the position with vial number "2". Such a sequence makes it possible to minimize the number of times to change a parameter that needs a considerable time to be set (e.g. temperature), or decrease the number of cleaning operations to save time, solutions and other resources.

For comparison with the conventional technique, FIG. 6A shows an example of the analysis schedule table in which the continuous analysis using the three analysis methods of "Method_A", "Method_C" and "Method_M" is exhaustively performed. In this case, an analysis using an analysis method which is not suitable for analyzing the target compounds contained in a given specimen is also performed, so that the number of analyses increases. By comparison, in the case of the LC-MS analyzing system of the present embodiment, an analysis using an analysis method which is not suitable for analyzing the target compounds contained in a given specimen is omitted. Therefore, no useless analysis is performed and the number of analyses becomes smaller.

As described to this point, the LC-MS analyzing system of the present embodiment can automatically select suitable analysis methods for the target compounds specified in the specimen information and create an analysis schedule table, without requiring the operator to perform troublesome tasks. Therefore, there is no possibility of incorrect operations by the operator. The continuous analysis can be efficiently performed, so that the period of time required for the analysis can be shortened as compared to the conventional case. The present system is also effective for the cost reduction of the analysis since it prevents both the waste of specimen and the wasteful consumption of the mobile phase in LC-MS unit 1.

The analyzing efficiency of the LC-MS analyzing system of the present embodiment can be further improved by additionally incorporating the following function into the control unit 3.

As described earlier, the analysis method in the LC-MS analyzing system shown in FIG. 1 includes, as one of the analysis conditions, the retention time at which the target compound is eluted from the column 14 under the LC separation conditions described in the analysis method. As noted earlier, in many cases, LC separation conditions differ from compound to compound. However, in some cases, a completely identical set of LC separation conditions is specified for a plurality of compounds. In such a case, if the retention times of those compounds are not overlapped (more practically, if there is no overlapping of their "retention-time ranges" defined at the respective retention times with a specific time width), those compounds can be detected by a single analysis.

Accordingly, the used-method automatic determiner 34 checks the content (analysis conditions and their parameters) of the plurality of selected and indicated analysis methods. If there are two or more analysis methods including the same set of LC separation conditions, the analysis conditions described in those analysis methods are merged into a temporary analysis method with a plurality of compounds as the target. If all compounds included in this temporary analysis method are specified as the target compounds in one specific specimen, this temporary analysis method is selected as the suitable analysis method for that specimen. For example, if this technique is applied to the case of FIG. 6B, there is the possibility that one specimen contained in a vial with one vial number which requires the analysis to be performed two times using different analysis methods can be analyzed by a single analysis using one temporary analysis method. If the retention times of those target compounds are not overlapped, those target compounds can be individually detected without any mutual influence, so that the extracted ion chromatogram corresponding to each target compound can be created. With this chromatogram, the quantity of each target compound can be correctly determined.

Although the previously described embodiment is concerned with the analyzing-device controller applied in an LC-MS, the present invention can also be applied not only in the LC-MS but also in the LC, GC and GC-MS as well as various other types of analyzing devices.

It is also evident that any change, modification or addition appropriately made within the spirit of the present invention in any other respect than those already described will also fall within the scope of claims of the present application.

REFERENCE SIGNS LIST

1 . . . Liquid Chromatograph Mass Spectrometer (LC-MS) Unit
11 . . . Mobile Phase Container
12 . . . Pump
13 . . . Injector
14 . . . Column
15 . . . Tandem Quadrupole Mass Spectrometer
2 . . . Auto-Sampler
21 . . . Sample Plate
22 . . . Vial
23 . . . Plate Driver
24 . . . Sample Collector
3 . . . Control Unit
30 . . . Analysis Controller
31 . . . Analysis Method Creation Processor
32 . . . Method Information Creation Processor
33 . . . Sample Registration Processor
34 . . . Used-Method Automatic Determiner
35 . . . Analysis Schedule Creator
36 . . . Storage Unit
361 . . . Specimen Information Storage Section
362 . . . Analysis Method Storage Section
363 . . . Method Information Storage Section
364 . . . Analysis Schedule Storage Section
4 . . . Input Unit
5 . . . Display Unit

The invention claimed is:

1. An analyzing-device, comprising:
an analyzing device unit that performs a continuous analysis of a plurality of specimens, each of the specimens containing one or a plurality of compounds, by separating the compounds and detecting the separated compounds, the analyzing device unit being a liquid chromatograph; and
an analyzing-device controller for controlling an operation of the analyzing device unit for performing the continuous analysis, the analyzing-device controller including:
a) a specimen information obtainer for obtaining and memorizing, for each specimen to be analyzed, specimen information showing a correspondence relationship between an information identifying the specimen and one or a plurality of possible target compounds contained in the specimen;
b) a method information obtainer for obtaining, for each analysis method in which analysis conditions for performing an analysis are described, a piece of information included in the analysis method, this information showing a compound assumed in an analysis using the analysis method, and for creating and memorizing method information linking the compound with the analysis method;
c) an optimum method determiner configured as follows: when a plurality of specimens to be actually analyzed are specified by an operator in a continuous analysis for a plurality of specimens, the optimum method determiner identifies one or a plurality of target compounds in each of the specified specimens based on the specimen information memorized by the specimen information obtainer, then identifies one or a plurality of analysis methods for the one or the plurality of target compounds identified for each of the specimens based on the method information memorized by the method information obtainer, and creates combination information linking the plurality of specimens specified by the operator with one or a plurality of analysis methods suitable for use in an analysis for each of the plurality of specimens; and
d) an analysis method integrator configured as follows: when a plurality of analysis methods are linked with a same specimen as a result of the processing performed by the optimum method determiner, the analysis method integrator checks that separation conditions in the liquid chromatograph included in each of those analysis methods are common to all analysis methods, and retention times of the plurality of target compounds corresponding to those analysis methods are not overlapped; and if these facts are confirmed, the analysis method integrator combines the separation conditions included in those analysis methods to create a temporary analysis method corresponding to the plurality of target compounds,
wherein the analyzing-device controller controls the analyzing device unit so that the analyzing device unit performs continuous analysis on the plurality of specimens by separating compounds of each of the plurality of specimens and detecting the separated compounds based on the information created by the optimum method determiner.

2. The analyzing-device according to claim 1, wherein:
when the target compounds contained in each of the plurality of specimens specified as a target of the analysis include at least one target compound for which no corresponding analysis method is present and at least one target compound for which a corresponding analysis method is present, an alert notification is made while the analysis for the this target compound in the specimen concerned is performed, and when none of the target compounds have a corresponding analysis method, an error notification is made.

3. The analyzing-device according to claim 1, wherein:
the information identifying each specimen is at least one character indicating each specimen from among the plurality of specimens.

* * * * *